United States Patent
Starkenmann

(10) Patent No.: US 6,734,158 B2
(45) Date of Patent: May 11, 2004

(54) HETERO SPIRO COMPOUND AS PERFUMING AND FLAVORING INGREDIENT

(75) Inventor: Christian Starkenmann, Onex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/366,518

(22) Filed: Feb. 14, 2003

(65) Prior Publication Data

US 2003/0175395 A1 Sep. 18, 2003

(30) Foreign Application Priority Data

Mar. 8, 2002 (WO) ............................... PCT/IB02/00730

(51) Int. Cl.[7] .............................. A61K 7/46; A23L 1/221
(52) U.S. Cl. ............................... 512/12; 512/8; 512/9; 512/11; 512/13; 512/25; 426/650
(58) Field of Search ............................ 512/8, 9, 11, 12, 512/13, 25; 426/650

(56) References Cited

PUBLICATIONS

Katsumi Umano et al, "Volatile Chemicals Formed in the Headspace of a Heated D–Glucose L–Cysteine Maillard Model System", America Chemical Society, Journal Agricultural Food Chem., vol. 43, pp. 2212–2218 (1995).

Akio Yasuhara et al., "Gas Chromatographic/Mass Spectrometric Method for Analysis of Trace Carbonyl Compounds in Foods and Beverages", America Chemical Society, Journal Agricultural Food Chem., vol. 46, pp. 2664–2670 (1998).

*Primary Examiner*—Jill Warden
*Assistant Examiner*—Monique T. Cole
(74) *Attorney, Agent, or Firm*—Winston & Strawn LLP

(57) ABSTRACT

The present invention relates to the perfume and flavor industry. It concerns more particularly the use as perfuming or flavoring ingredient of 6-methyl-7-oxa-1-thia-4-azaspiro[4.4]nonane, of formula

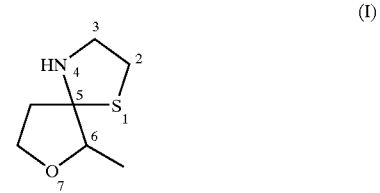

(I)

The invention also relates to the perfumed or flavored consumer products or perfuming or flavoring compositions containing as active ingredient a compound of formula (I).

8 Claims, No Drawings

HETERO SPIRO COMPOUND AS PERFUMING AND FLAVORING INGREDIENT

BACKGROUND ART

The present invention relates to the perfume and flavor industry. It concerns more particularly the use as perfuming or flavoring ingredient of 6-methyl-7-oxa-1-thia-4-azaspiro[4.4]nonane The 6-methyl-7-oxa-1-thia-4-azaspiro[4.4]nonane has been cited twice in the prior art (T. Shibamoto et al. in *J. Agric. Food. Chem.*, 1995, 43, 2664 or in *J. Agric. Food. Chem.*, 1998, 46, 2212)

In its first paper, the author discloses only that 6-methyl-7-oxa-1-thia-4-azaspiro[4.4]nonane is one of the many volatile products present in a mixture obtained by the Maillard reaction between pure D-glucose and pure L-cysteine.

In the second reference, the author reports a synthesis and the mass spectras of a series of thiazolidine derivatives, including 6-methyl-7-oxa-1-thia-4-azaspiro[4.4]nonane, with the aim of building a mass spectra library of said compounds.

However in said documents there is no mention or suggestion of any organoleptic properties of the specific compounds of formula (I), or of any potential use of said compounds as perfuming or flavoring ingredients. Perfuming compositions containing said products are not disclosed either.

SUMMARY OF THE INVENTION

The present invention is directed towards a method to confer, enhance, improve or modify the odor or flavor properties of a perfuming or flavoring composition or of a perfumed or flavored article, which method comprises adding to the composition or article an effective amount of 6-methyl-7-oxa-1-thia-4-azaspiro[4.4]nonane.

Another aspect of the invention provides perfumed or flavored consumer product or perfuming or flavoring compositions comprising as active ingredient 6-methyl-7-oxa-1-thia-4-azaspiro[4.4]nonane.

DETAILED DESCRIPTION OF PREFERRED EMBODIMENTS

Surprisingly, we have now established that 6-methyl-7-oxa-1-thia-4-azaspiro[4.4]nonane, of formula

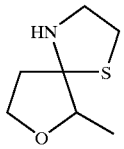

(I)

possesses surprising organoleptic properties which have been found to be particularly useful and appreciated for the preparation of perfumes, perfuming compositions and perfumed consumer product, as well as for the preparation of flavors, flavoring compositions and flavored consumer product.

The 6-methyl-7-oxa-1-thia-4-azaspiro[4.4]nonane is much appreciated by perfumers for its odor which is cereal-like and remarkably natural, having cracker and pop-corn notes, together with an excellent roasted coffee character and basmati rice type bottom note. Said odor, which is quite unusual for a perfumery ingredient, brings an interesting and original cereal-like connotation to the modern perfumery.

Furthermore, 6-methyl-7-oxa-1-thia-4-azaspiro[4.4]nonane and its isomers have also the advantage to be surprisingly stable in all the types of perfumery media.

As anticipated above, the compounds of formula (I) are also useful as flavoring ingredients, i.e. to impart taste to flavoring compositions and foods or beverages. For instance 6-methyl-7-oxa-1-thia-4-azaspiro[4.4]nonane is able to impart nutty, praline and hazelnut flavor notes.

The invention concerns the use of 6-methyl-7-oxa-1-thia-4azaspiro[4.4]nonane as perfuming or flavoring ingredients, in other words it concerns a method to confer, enhance, improve or modify the odor or flavor properties of a perfuming or flavoring composition or of a perfumed or flavored consumer article, which method comprises adding to said composition or article an effective amount of 6-methyl-7-oxa-1-thia-4-azaspiro [4.4]nonane. By "use of 6-methyl-7-oxa-1-thia-4-azaspiro[4.4]nonane" it has to be understood here the use of the compound in any of its forms which can be advantageously employed in perfumery or in flavors. Such forms include the compound itself or a composition of matter consisting of a compound of formula (I) and a solvent commonly used in perfumery or in flavors. As examples of said solvents used in perfumery, one can cite compounds such as dipropyleneglycol, diethyl phthalate, isopropyl myristate, benzyl benzoate, 2-(2-ethoxyethoxy)-1-ethanol or ethyl citrate, which are the most commonly used. As examples of solvents commonly used in flavors, one can cite compounds such as propylene glycol, triacetine, triethyl citrate, benzylic alcohol, benzyl benzoate, ethanol, vegetal oils or terpenes.

Additionally, the present invention concerns a perfuming composition comprising the compound of formula (I). Generally speaking, by "perfuming composition" we mean here a mixture or composition comprising at least two perfuming ingredients, in any of their forms, and possibly one or more solvents commonly used in perfuming compositions. Therefore, a perfuming composition according to the invention is a composition comprising an olfactive effective amount of the invention's compound, together with one or more perfuming co-ingredients and possibly one or more solvents commonly used in perfumery.

The nature and type of these perfuming co-ingredients do not warrant a more detailed description here, which in any case would not be exhaustive, the skilled person being able to select them on the basis of its general knowledge and according to the nature of the product to be perfumed and the desired olfactory effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils of natural or synthetic origin. Many of these ingredients are in any case listed in reference texts such as the book by S. Arctander, Perfume and Flavor Chemicals, 1969, Montclair, N.J., U.S.A., or its more recent versions, or in other works of a similar nature, as well as in the abundant patent literature in the field of perfumery.

Similarly, a detailed description of the nature and type of solvents commonly used in perfuming compositions cannot be exhaustive. A skilled person in the art is able to select them on the basis of the nature of the product to be perfumed. However, as non-limiting examples of such solvents, one can cite, in addition to the solvents mentioned above, also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

It is also understood that any composition resulting from a chemical synthesis in which the compound of the invention is involved as a starting intermediate or as an end-product is not a perfuming composition according to the invention.

The perfuming compositions according to the invention may be in the form of a simple mixture of the various co-ingredients and solvents, or also in the form of a bi-phasic system such as an emulsion or microemulsion. Such systems are well known to a person skilled in the art.

As previously mentioned, 6-methyl-7-oxa-1-thia-4-azaspiro[4.4]nonane, in any of its forms, or a perfuming composition comprising said compound, is a useful perfuming ingredient which can be advantageously used in all the fields of modern perfumery such as fine perfumery or functional perfumery to obtain perfumed consumer products. Such perfumed consumer products, which include a consumer article comprising an olfactive effective amount of the invention's compound, in any of its forms, are also an object of the present invention.

Suitable consumer articles comprise solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned articles may represent an aggressive medium for the invention's compound, so that it may be necessary to protect the latter from premature degradation, for example by encapsulation.

For the sake of clarity, it has to be mentioned that, by "perfumed consumer product", we mean here a consumer article that includes an olfactive effective amount of the invention's compound, possibly together with one or more perfuming co-ingredients and possibly one or more solvents commonly used in perfumery. By "consumer article" we mean here a consumable article comprising at least a part of the whole formulation corresponding to the desired article, e.g. a detergent or a perfume.

The nature and type of the constituents of the consumer article do not warrant a more detailed description here, which in any case would not be exhaustive, the skilled person being able to select them on the basis of its general knowledge and according to the nature and the desired effect of said article.

The proportions in which the compound according to the invention can be incorporated into the various aforementioned articles or compositions vary within a wide range of values. These values are dependent on the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations from 0.01% to 2.0%, and preferably from 0.1% to 0.5%, by weight of this compound, with respect to the perfuming composition in which they are incorporated, can be typically used. Lower concentrations than these can be used when this compound is directly applied for perfuming some of the consumer products mentioned above.

As mentioned above, the compound of the invention, in any of its forms, can also be incorporated into flavoring compositions or flavored consumer products, e.g. to impart, or modify, a taste. For the sake of clarity, by flavoring compositions or flavored articles we mean here compositions or articles as defined above and wherein the term perfuming or perfumed is replaced by flavoring or flavored. Consequently, a flavoring composition comprising a flavor effective amount of the invention's compound, together with one or more flavoring co-ingredients and possibly one or more solvents commonly used in flavors, is also an embodiment of the present invention.

Examples of flavoring co-ingredients are listed in reference texts such as the above-mentioned book by S. Arctander, as well as in the abundant patent literature in the field of flavors. The skilled person in the art of flavors is able to select them on the basis of its general knowledge and according to the nature of the product to be flavored and the desired taste. Examples of solvents commonly used in the flavor industry are the same as listed above.

As previously, its is also understood that any composition resulting from a chemical synthesis in which the compound of the invention is involved as a starting intermediate or as an end-product is not a flavoring composition according to the invention.

The flavoring compositions according to the invention may be in the form of a simple mixture of flavoring ingredients or also in an encapsulated form, i.e. a flavoring composition entrapped into a solid matrix which may comprise wall-forming and plasticizing materials such as mono, di- or trisaccharides, natural or modified starches, hydrocolloids, cellulose derivatives, polyvinyl acetates, polyvinylalcohols, proteins or pectins. Examples of particularly useful matrix materials include sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Other suitable carrier ingredients are cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996 Said encapsulation is well known to a person skilled in the art, and may be performed, for instance, using techniques such as spray-drying, agglomeration or yet extrusion; or consists of a coating encapsulation, including coacervation and complex coacervation techniques.

Another embodiment of the present invention is a flavored consumer product comprising a foodstuff, or a beverage, including a flavor effective amount of the invention's compound, in any of its forms. Of course, said foodstuff or beverage may also include one or more flavoring co-ingredients and possibly one or more solvents commonly used in flavors.

Suitable foodstuffs or beverages include bakery products, yogurts or other dairy products, sauces or ready cooked dishes and sweet goods such as desserts, ice-creams, candies, compotes or fruit jams.

When the invention's compounds are used for these compositions or consumer articles, useful flavor effects can be obtained using concentrations of the order of 0.1 to 100 ppm, more preferably in the order of 1 to 50 ppm, with respect to the product into which they are incorporated. Much higher concentrations can be chosen when the compounds are used in concentrated flavors or flavoring compositions intended to be incorporated in consumer products.

The compound of the invention thus makes it possible to confer, improve, enhance or modify the odor or taste of consumer products, as well as of perfuming bases or concentrates, or yet flavor preparations and compositions. In other words, it can impart to the latter its characteristic organoleptic properties, as the case may be, thus modifying and/or improving the original odor and taste properties of the products and compositions in which they are incorporated

EXAMPLES

The invention will now be described in further detail by way of the following examples, wherein the temperatures are indicated in degrees centigrade (° C.); the NMR spectral data were recorded with a 360 MHz machine in $CDCl_3$; the chemical displacement δ are indicated in ppm with respect to the TMS as standard and all the abbreviations have the usual meaning in the art.

Example 1

Synthesis of 6-methyl-7-oxa-1-thia-4-azaspiro[4.4] Nonane

To 15.4 g of 2-aminoethanethiol-HCl (0.13 mole) dissolved into 50 ml of water were added slowly 20 g of 2-methyl-3-tetrahydrofuranone (0.2 mole) (solution pH=2.7). The pH was kept to neutrality by adding 10% aqueous NaOH. After 1 hour, extraction of the water solution with $Et_2O$, drying of the organic phase with $MgSO_4$ and distillation of the crude product (Bp 1.7 mbar, 93°–96° C.) gave 18 g of the desired product (yield=90%). The product was obtained as a mixture of two diastereoisomers (isomers a and b).

$^1$H-NMR: 1.24(d, J=6.5, 3H, 56%; isomer a); 1.26(d, J=6.5, 3H, 44%; isomer b); 1.7(broad, 1H); 2.12–2.23(m, 1H); 2.30–2.41(m, 1H); 2.87–3.06(m, 2H); 3.19–3.39(m, 2H); 3.81–4.1(m, 3H).

$^{13}$C-NMR: 86.4–83.7(s); 81.2–81.9(d); 65.8–65.5(t); 52.2–51.1(t); 43.3–41.4(t); 36.2–36.0(t); 13.3–19.6(q).

MS: Isomer a: 159((M+H)$^+$; 25), 130(10), 116(20), 115 (96), 114(100), 87(10), 62(20), 60(25), 54(15), 43(10).

Isomer b : 159((M+H)$^+$; 25), 130(10), 116(20), 115(100), 114(98), 87(10), 62(20), 60(25), 54(15), 43(10).

Example 2

Preparation of a Perfuming Composition

A woman perfume base composition of the type "Oriental" was prepared by admixing the following ingredients:

| Ingredient | Parts by weight |
| --- | --- |
| Benzyl acetate | 30 |
| Cinnamyl acetate | 10 |
| Geranyl acetate | 10 |
| Linalyl acetate | 100 |
| 10%* Cis-3-hexanol acetate | 10 |
| 3-Phenyl-1-propanol | 30 |
| 1%* Dodecanal | 30 |
| 10%* Allyl amyl glycolate | 40 |
| 10%* Methyl anthranilate | 10 |
| 1,4-Dioxa-5,17-cycloheptadecanedione | 30 |
| Bergamot essential oil | 200 |
| 4-Hydroxy-3-methoxybenzaldehyde | 40 |
| CASHMERAN ®[1] | 30 |
| Sfuma lemon essential oil | 150 |
| Citronellol | 20 |
| Coumarine | 120 |
| Tarragon essential oil | 20 |
| (1'R,2R)-2-Methyl-4-(2',2',3'-trimethyl-3'-cyclopenten-1'-yl)-4-penten-1-ol | 50 |
| GALAXOLIDE ®[2] 50 MIP | 100 |
| Geraniol | 10 |
| HEDIONE ® HC[3] | 130 |
| Heliopropanal | 10 |
| 10%* Indol | 10 |
| Lavander essential oil | 30 |
| Linalool | 50 |
| Sfuma mandarine essential oil | 40 |
| Crystal moss | 20 |
| 10%* Muscenone Delta[4] | 60 |
| Patchouli essential oil | 60 |
| Cedrenyl acetate | 50 |
| Santal essential oil | 50 |
| 10% Tagete essential oil | 50 |
| 1%* Undecalactone gamma | 30 |
| 10%* Triplal[2] | 30 |
| Terpineol alpha | 10 |
| 4,7,11,11-Tetramethyl-tricyclo[5.4.0.0(1,3)]undecan-5-one | 50 |
| Vanilline | 150 |
| Vetyver | 30 |
| Vulcanolide ®[5] | 10 |
| Armoise[6] | 30 |
| 10%* White thyme[6] | 40 |
| Total | 1980 |

*in diproypleneglycol
[1]1,2,3,5,6,7-hexahydro-1,1,2,3,3-pentamethyl-4-indenone; origin: IFF, U.S.A.
[2]origin: IFF, U.S.A.
[3]methyl dihydrojasmonate; origin: Firmenich SA, Geneva, Switzerland
[4]3-methyl-(4 and 5)-cyclopentadecen-1-one; origin: Firmenich SA, Geneva, Switzerland
[5]5,6,7,8-Tetrahydro-3,5,5,6,7,8,8-heptamethyl-2-naphthalenecarbaldehyde; origin: Firmenich SA, Geneva, Switzerland
[6]Artificial base; origin: Firmenich SA, Geneva, Switzerland The addition of 20 parts by weight of 6-methyl-7-oxa-1-thia-4-azaspiro[4.4]nonane, diluted to 10% in dipropyleneglycol, to the above-described oriental base provided to the latter a unique cereal-like connotation and at the same time imparted also lift and warmth by developing the sweet vanilla note.

Example 3

Preparation of a Perfuming Composition

An "rice" type composition was prepared by admixing the following ingredients:

| Ingredient | Parts by weight |
|---|---|
| Benzaldehyde | 20 |
| 10%* Aldehyde C6 | 30 |
| Cuminic aldehyde | 100 |
| Caraway essential oil | 30 |
| Caryophyllene | 30 |
| 4-Cyclohexyl-2-methyl-2-butanol | 200 |
| Coumarine | 300 |
| 1%* Ethyl praline | 340 |
| HEDIONE ® HC[1] | 100 |
| HELVETOLIDE ®[2] | 400 |
| KOUMALACTONE ®[3] | 100 |
| 6-Methyl-5-hepten-2-one | 20 |
| 10%* Methylpentylketone | 50 |
| Muscenone Delta[4] | 50 |
| Nonalactone gamma | 50 |
| ROMANDOLIDE [5] | 150 |
| 10%* Vanilline | 20 |
| Total | 1990 |

*in dipropyleneglycol
[1] methyl dihydrojasmonate; origin: Firmenich SA, Geneva, Switzerland
[2] (+)-(1S,1'R)-2-[1-(3',3'-dimethyl-1'-cyclohexyl)ethoxy]-2-methylpropylpropanoate; origin: Firmenich SA, Geneva, Switzerland
[3] Perhydro-3,6-dimethyl-benzo[B]furan-2-one; origin: Firmenich SA, Geneva, Switzerland
[4] 3-methyl-(4 and 5)-cyclopentadecen-1-one; origin: Firmenich SA, Geneva, Switzerland
[5] (1S,1'R)-[1-(3',3'-dimethyl-1'-cyclohexyl)ethoxycarbonyl]methyl propanoate; origin: Firmenich SA, Geneva, Switzerland The addition of 10 parts by weight of 6-methyl-7-oxa-1-thia-4-azaspiro[4.4]nonane to the above-described composition imparted to the latter a very distinct basmati rice, roasted cereal effect. Said olfactory effect was at the same time more natural and less roasted, amine and vitamin that the one obtained by adding the acetylpyrazine.

Example 4

Preparation of a Perfuming Composition

A "milk" type base composition was prepared by admixing the following ingredients:

| Ingredient | Parts by weight |
|---|---|
| Benzyl acetate | 10 |
| Coumarine | 20 |
| 1%* Diacetyl | 20 |
| dodecalactone delta | 300 |
| Ethyl praline | 300 |
| Ethylvanilline | 10 |
| GALAXOLIDE ®[1] 50 MIP | 1950 |
| HEDIONE ® HC[2] | 20 |
| Heliotropine | 20 |
| HELVETOLIDE ®[3] | 500 |
| Irone alpha | 100 |
| 1%* KOUMALACTONE ®[4] | 270 |
| LYRAL ®[5] | 30 |
| Muscenone Delta[6] | 130 |
| ROMANDOLIDE ®[7] | 1000 |
| 10%* 2-(4-Methyl-1,3-thiazol-5-yl)-1-ethanol | 150 |
| Undecalactone gamma | 50 |
| Vanilline | 20 |
| 10%* Ionone beta | 20 |
| (1S,2S,3S)-2,6,6-Trimethyl-bicyclo[3.1.1]heptane-3-spiro-2'-cyclohexen-4'-one | 10 |
| Rose[8] | 20 |
| Total | 4950 |

*in dipropyleneglycol
[1] origin: IFF, USA
[2] methyl dihydrojasmonate; origin: Firmenich SA, Geneva, Switzerland
[3] (+)-(1S,1'R)-2-[1-(3',3'-dimethyl-1'-cyclohexyl)ethoxy]-2-methylpropylpropanoate; origin: Firmenich SA, Geneva, Switzerland
[4] Perhydro-3,6-dimethyl-benzo[B]furan-2-one; origin: Firmenich SA, Geneva, Switzerland
[5] 4-(4-hydroxy-4-methyl-pentyl)-3-cyclohexene-1-carbaldehyde; origin: IFF, U.S.A.
[6] 3-methyl-(4 and 5)-cyclopentadecan-1-one; origin: Firmenich SA, Geneva, Switzerland
[7] (1S,1'R)-[1-(3',3'-dimethyl-1'-cyclohexyl)ethoxycarbonyl]methyl propanoate; origin: Firmenich SA, Geneva, Switzerland
[8] Artificial base; origin: Firmenich SA, Geneva, Switzerland The addition of 50 parts by weight of 6-methyl-7-oxa-1-thia-4-azaspiro[4.4]nonane to the above-described base composition imparted to the latter a nice roasted coffee connotation and changes the olfactory note of the base from a milky note to a coffee with milk note.

What is claimed is:

1. A perfuming composition comprising an olfactive effective amount of 6-methyl-7-oxa-1-thia-4-azaspiro[4.4]nonane, together with one or more perfuming co-ingredients and possibly one or more solvents commonly used in perfumery.

2. A perfumed consumer product comprising a consumer article that include an olfactive effective amount of 6-methyl-7-oxa-1-thia-4-azaspiro[4.4]nonane, possibly together with one or more perfuming co-ingredients and possibly one or more solvents commonly used in perfumery.

3. A perfumed consumer product according to claim 2, wherein the consumer article is a solid or liquid detergent, a fabric softener, a perfume, a cologne or after-shave lotion, a perfumed soap, a shower or bath salt, mousse, oil or gel, a hygiene product or hair care product, a shampoo, a body-care product, a deodorant or antiperspirant, an air freshener, a cosmetic preparation, a fabric refresher, an ironing water, papers, wipes or bleaches.

4. A flavoring composition comprising an flavor effective amount of 6-methyl-7-oxa-1-thia-4-azaspiro[4.4]nonane, together with one or more flavoring co-ingredients and possibly one or more solvents commonly used in flavors; provided that the mixture obtained by the Maillard reaction between pure D-glucose and pure L-cysteine is excluded.

5. A flavored consumer product comprising a foodstuff or beverage that includes a flavor effective amount of 6-methyl-7-oxa-1-thia-4-azaspiro[4.4]nonane; provided that the mixture obtained by the Maillard reaction between pure D-glucose and pure L-cysteine is excluded.

6. A flavored consumer product according to claim 5, wherein the foodstuff is a bakery product, yogurt or other dairy product, sauce or ready cooked dish, sweet good, dessert, ice-cream, candy, compote or fruit jam.

7. A method to confer, enhance, improve or modify the odor properties of a composition or of a perfumed article, which method comprises adding to said composition or article an olfactive effective amount of 6-methyl-7-oxa-1-thia-4-azaspiro [4.4]nonane, in any of its forms.

8. A method to confer, enhance, improve or modify the flavor properties of a composition or foodstuff or beverage product, which method comprises adding to said composition or product a flavor effective amount of 6-methyl-7-oxa-1-thia-4-azaspiro [4.4]nonane, in any of its forms.

* * * * *